US010532139B2

(12) United States Patent
Medina et al.

(10) Patent No.: US 10,532,139 B2
(45) Date of Patent: Jan. 14, 2020

(54) SHORT-RANGE WIRELESS COMMUNICATION FOR A DIALYSIS SYSTEM

(71) Applicant: Fresenius Medical Care Holdings, Inc., Waltham, MA (US)

(72) Inventors: Carlos E. Medina, Concord, CA (US); David Yuds, Antioch, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 727 days.

(21) Appl. No.: 14/865,461

(22) Filed: Sep. 25, 2015

(65) Prior Publication Data
US 2017/0087290 A1    Mar. 30, 2017

(51) Int. Cl.
*A61M 1/16* (2006.01)
*A61M 1/28* (2006.01)
(Continued)

(52) U.S. Cl.
CPC .......... *A61M 1/1603* (2014.02); *A61M 1/282* (2014.02); *G16H 20/40* (2018.01); *G16H 40/63* (2018.01); *H04B 5/0031* (2013.01); *H04W 4/80* (2018.02); *A61M 1/1613* (2014.02); *A61M 2205/3561* (2013.01); *A61M 2205/3569* (2013.01); *A61M 2205/3584* (2013.01); *A61M 2205/52* (2013.01); *A61M 2205/6009* (2013.01); *A61M 2205/6018* (2013.01)

(58) Field of Classification Search
CPC .. A61M 1/1603; A61M 1/282; A61M 1/1613; A61M 1/16; A61M 1/28; A61M 2205/3561; A61M 2205/3669; A61M 2205/3584; A61M 2205/52; A61M 2205/6009; A61M 2205/6018
USPC ....................................................... 210/646
See application file for complete search history.

(56) References Cited

U.S. PATENT DOCUMENTS 3,352,779 A * 11/1967 Austin ................ A61M 1/1656
                                                                    137/5
5,822,544 A * 10/1998 Chaco ................. G06F 19/3418
                                                                    705/2
(Continued)

FOREIGN PATENT DOCUMENTS

| WO | WO 2011/028261 A2 | 3/2011 |
| WO | WO 2014/004448 A1 | 1/2014 |
| WO | WO2016144541 A1 | 9/2016 |

OTHER PUBLICATIONS

U.S. Appl. No. 14/640,364, filed Mar. 6, 2015, Arizza.
(Continued)

Primary Examiner — Robert Clemente
Assistant Examiner — Akash K Varma
(74) Attorney, Agent, or Firm — Fish & Richardson P.C.

(57) ABSTRACT

A dialysis system comprising: a dialysis machine; a communication module configured to communicate using a short-range wireless technology protocol; data storage configured to store data corresponding to identities of one or more short-range wireless devices; and a processor configured to: identify presence of a short-range wireless device; and cause the dialysis machine to carry out an action when one or both of i) the presence of the short-range wireless device is identified, and ii) the presence of the short-range wireless device is no longer identified.

32 Claims, 5 Drawing Sheets

(51) Int. Cl.
*H04B 5/00* (2006.01)
*H04W 4/00* (2018.01)
*H04W 4/80* (2018.01)
*G16H 40/63* (2018.01)
*G16H 20/40* (2018.01)

(56) References Cited

U.S. PATENT DOCUMENTS

| | | |
|---|---|---|
| 6,673,314 B1 | 1/2004 | Burbank et al. |
| 7,033,539 B2 | 4/2006 | Krensky et al. |
| 7,044,927 B2 | 5/2006 | Mueller et al. |
| 7,699,806 B2 | 4/2010 | Ware et al. |
| 8,190,651 B2 | 5/2012 | Treu et al. |
| 8,313,642 B2 | 11/2012 | Yu et al. |
| 8,315,885 B2 | 11/2012 | Krogh et al. |
| 8,449,471 B2 | 5/2013 | Tran |
| 8,549,600 B2 | 10/2013 | Shedrinsky |
| 8,776,246 B2 | 7/2014 | Allegri et al. |
| 8,871,095 B2 | 10/2014 | Yu et al. |
| 8,905,959 B2 | 12/2014 | Basaglia |
| 8,909,613 B2 | 12/2014 | Treu et al. |
| 8,996,393 B2 | 3/2015 | Sobie |
| 2009/0275881 A1 | 11/2009 | Lo et al. |
| 2011/0093294 A1 | 4/2011 | Elahi et al. |
| 2012/0003933 A1 | 1/2012 | Baker et al. |
| 2012/0212455 A1* | 8/2012 | Kloeffel ............... A61M 1/14 345/175 |
| 2012/0297255 A1* | 11/2012 | Case ................ G06F 19/322 714/47.1 |
| 2013/0138452 A1 | 5/2013 | Cork et al. |
| 2013/0141329 A1 | 6/2013 | Halbert et al. |
| 2013/0310726 A1 | 11/2013 | Miller et al. |
| 2013/0346102 A1 | 12/2013 | Yu et al. |
| 2014/0006510 A1 | 1/2014 | Hamilton et al. |
| 2014/0148104 A1* | 5/2014 | Marterstock ........... A61M 1/14 455/73 |
| 2014/0276375 A1 | 9/2014 | Minkus |
| 2014/0288947 A1 | 9/2014 | Simpson et al. |
| 2015/0011970 A1 | 1/2015 | Kamen et al. |
| 2015/0095041 A1* | 4/2015 | Kim ................... G06F 19/3418 705/2 |

OTHER PUBLICATIONS

Notification of Transmittal of the International Search Report and the Written Opinion of the International Searching Authority for corresponding PCT Application No. PCT/US2016/050366, dated Nov. 28, 2016, 12 pages.

* cited by examiner

SHORT-RANGE WIRELESS COMMUNICATION FOR A DIALYSIS SYSTEM

TECHNICAL FIELD

This invention relates to wireless communication for dialysis systems.

BACKGROUND

Renal dysfunction or failure and, in particular, end-stage renal disease, causes the body to lose the ability to remove water and minerals and excrete harmful metabolites, maintain acid-base balance and control electrolyte and mineral concentrations within physiological ranges. Toxic uremic waste metabolites, including urea, creatinine, and uric acid, accumulate in the body's tissues which can result in a person's death if the filtration function of the kidney is not replaced.

Dialysis is commonly used to replace kidney function by removing these waste toxins and excess water. In one type of dialysis treatment—hemodialysis (HD)—toxins are filtered from a patient's blood externally in a hemodialysis machine. Blood passes from the patient through a dialyzer separated by a semi-permeable membrane from a large volume of externally-supplied dialysis solution. The waste and toxins dialyze out of the blood through the semi-permeable membrane into the dialysis solution, which is then typically discarded.

The dialysis solutions or dialysates used during hemodialysis typically contain sodium chloride and other electrolytes, such as calcium chloride or potassium chloride, a buffer substance, such as bicarbonate or acetate, and acid to establish a physiological pH, plus, optionally, glucose or another osmotic agent.

Another type of dialysis treatment is peritoneal dialysis (PD) that utilizes the patient's own peritoneum, a membranous lining of the abdominal body cavity. With its good perfusion properties, the peritoneum is capable of acting as a natural semi-permeable membrane for transferring water and waste products to a type of dialysate solution known as PD solution introduced temporarily into the patient's abdominal cavity. An access port is implanted in the patient's abdomen and the PD solution is infused usually by a pump into the patient's abdomen through a patient line and left to dwell for a period of time and then drained out. This procedure is usually repeated multiple times for a complete treatment. PD machines, such as Automated PD (APD) machines or PD cyclers, are designed to facilitate or control the PD process so that it can be performed at home without clinical staff in attendance.

Dialysis machines are typically equipped with interfaces for receiving inputs and providing information to users.

SUMMARY

A dialysis machine can be configured to identify presence of a short-range wireless device like an NFC-enabled ID card and then carry out a dialysis treatment when the presence of the short-range wireless device is identified.

In one aspect, a dialysis system includes a dialysis machine. The dialysis system also includes a communication module configured to communicate using a short-range wireless technology protocol. The dialysis system also includes data storage configured to store data corresponding to identities of one or more short-range wireless devices. The dialysis system also includes a processor configured to identify presence of a short-range wireless device. The processor is also configured to cause the dialysis machine to carry out an action when one or both of i) the presence of the short-range wireless device is identified, and ii) the presence of the short-range wireless device is no longer identified.

Implementations can include one or more of the following features.

In some implementations, the short-range wireless device includes a communication module configured to communicate with the communication module of the dialysis system.

In some implementations, the action includes initiating a dialysis treatment.

In some implementations, the processor is configured to identify one or more treatment parameters for the dialysis treatment based on the data corresponding to the identity of the short-range wireless device. The processor is also configured to cause the dialysis machine to carry out the dialysis treatment based on the identified one or more treatment parameters.

In some implementations, the dialysis machine is configured to operate a pump of the dialysis system. The action includes operation of the pump.

In some implementations, the treatment parameter includes one or more of a dialysate type, a dialysate fill volume, and a dialysate flow rate.

In some implementations, the processor is configured to determine that the presence of the short-range wireless device has ceased, and in response, automatically carry out the action.

In some implementations, the processor is configured to determine that the presence of the short-range wireless device has ceased before an expected termination of the action. The processor is also configured to, in response to determining that the presence of the short-range wireless device has ceased before the expected termination of the action, carry out an emergency procedure.

In some implementations, the action includes a dialysis treatment.

In some implementations, the emergency procedure includes one or both of pausing and ceasing the dialysis treatment.

In some implementations, the action includes stopping operation of a pump of the dialysis system.

In some implementations, the action includes initiating a disinfection procedure.

In some implementations, the action includes transmitting data representing information about a patient undergoing a dialysis treatment.

In some implementations, the data is transmitted to and stored on the short-range wireless device.

In some implementations, the dialysis system also includes a user interface module. The action includes causing the user interface module to prompt a user of the dialysis system to indicate whether to cease a dialysis treatment.

In some implementations, the short-range wireless device includes an identification card.

In some implementations, the dialysis machine includes a housing. The housing has a surface upon which the identification card can rest. The communication module is within the housing at a location substantially adjacent to the surface.

In some implementations, the identification card includes a photograph of a person associated with the identification card.

In some implementations, the communication module is configured to communicate using a Near-Field Communication (NFC) protocol.

In some implementations, the communication module is configured to communicate using an RFID protocol.

In some implementations, the communication module is configured to communicate using a Bluetooth™ protocol.

In some implementations, the data corresponding to identities of one or more short-range wireless devices include data representing a value stored on the short-range wireless device.

In some implementations, the data corresponding to identities of one or more short-range wireless devices include a portion of a patient record of a patient who will undergo a dialysis treatment.

In some implementations, the portion of the patient record includes the patient's name.

In some implementations, the dialysis system also includes a network communication module. The data storage is configured to receive the portion of the patient record by way of the network communication module. The portion of the patient record originates at a computer system of a medical facility.

In some implementations, the processor is configured to determine that the short-range wireless device corresponds to a medical supply associated with the dialysis treatment.

In some implementations, the dialysis treatment includes a hemodialysis treatment.

In some implementations, the dialysis treatment includes a peritoneal dialysis treatment.

In another aspect, a method of performing dialysis includes detecting, using a short-range wireless technology protocol, presence of a short-range wireless device. The method also includes determining that the short-range wireless device is associated with a patient. The method also includes causing a pump of a dialysis machine to administer a dialysis treatment to the patient. The method also includes automatically performing at least one action in response to one or both of i) determining that the short-range wireless device is present, and ii) determining that the short-range wireless device is no longer present.

Implementations can include one or more of the following features.

In some implementations, the short-range wireless device includes an identification card of the patient.

In some implementations, causing the pump to administer the dialysis treatment is the action that is automatically performed.

In some implementations, the action includes initiating a disinfection procedure.

In some implementations, the method also includes identifying one or more treatment parameters for the dialysis treatment based on the identity of the patient. The method also includes causing the pump to administer the dialysis treatment based on the identified one or more treatment parameters.

In some implementations, the method also includes transmitting data representing information about the patient.

In some implementations, the data is transmitted to and stored on the short-range wireless device.

Implementations can include one or more of the following advantages.

In some implementations, the systems and methods described herein can allow a user to easily provide information to the dialysis system without manually entering such information, thereby increasing efficiency and minimizing potential mistakes due to human error.

In some implementations, information that is typically manually entered following a treatment can be automatically transmitted and/or stored to a computer system, server, and/or database associated with the medical facility, thereby increasing efficiency and minimizing potential mistakes due to human error.

In some implementations, the dialysis machine automatically initiates a cleaning or disinfecting procedure upon removal of the ID card. In this way, dialysis machines can automatically be put in appropriate condition for a subsequent treatment without needing to receive a manual instruction.

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Medical devices (e.g., dialysis machines, dialysis machine components, dialysis machine accessories, etc.) can be configured to wirelessly communicate with other devices through a connection between the devices. A "connection" established between devices as described herein refers to electronic communication between two or more devices such that data can be communicated between the devices. The connection can be a unidirectional connection (in which data travels one way) or a bidirectional connection (in which data travels both ways).

A dialysis system can be configured to communicate with a portable device, such as an ID card (or another kind of card or device), using a connection established according to a short-range wireless technology protocol. One implementation of a short range wireless technology protocol is Near Field Communication (NFC) technology. The example of an ID card will be used throughout this description. When the ID card is introduced to or removed from proximity to the dialysis system, the dialysis system can perform one or more actions. For example, when the ID card is within a particular range of the dialysis system, the dialysis system can identify a user associated with the ID card and perform a dialysis treatment that is tailored to the particular user (e.g., a dialysis patient). When the ID card is removed from the particular range of the dialysis system, the dialysis system can perform an action such as initiating a disinfecting procedure, stopping/adjusting a treatment, or transmitting patient information (e.g., to a database and/or server associated with a medical facility).

Figure 1:
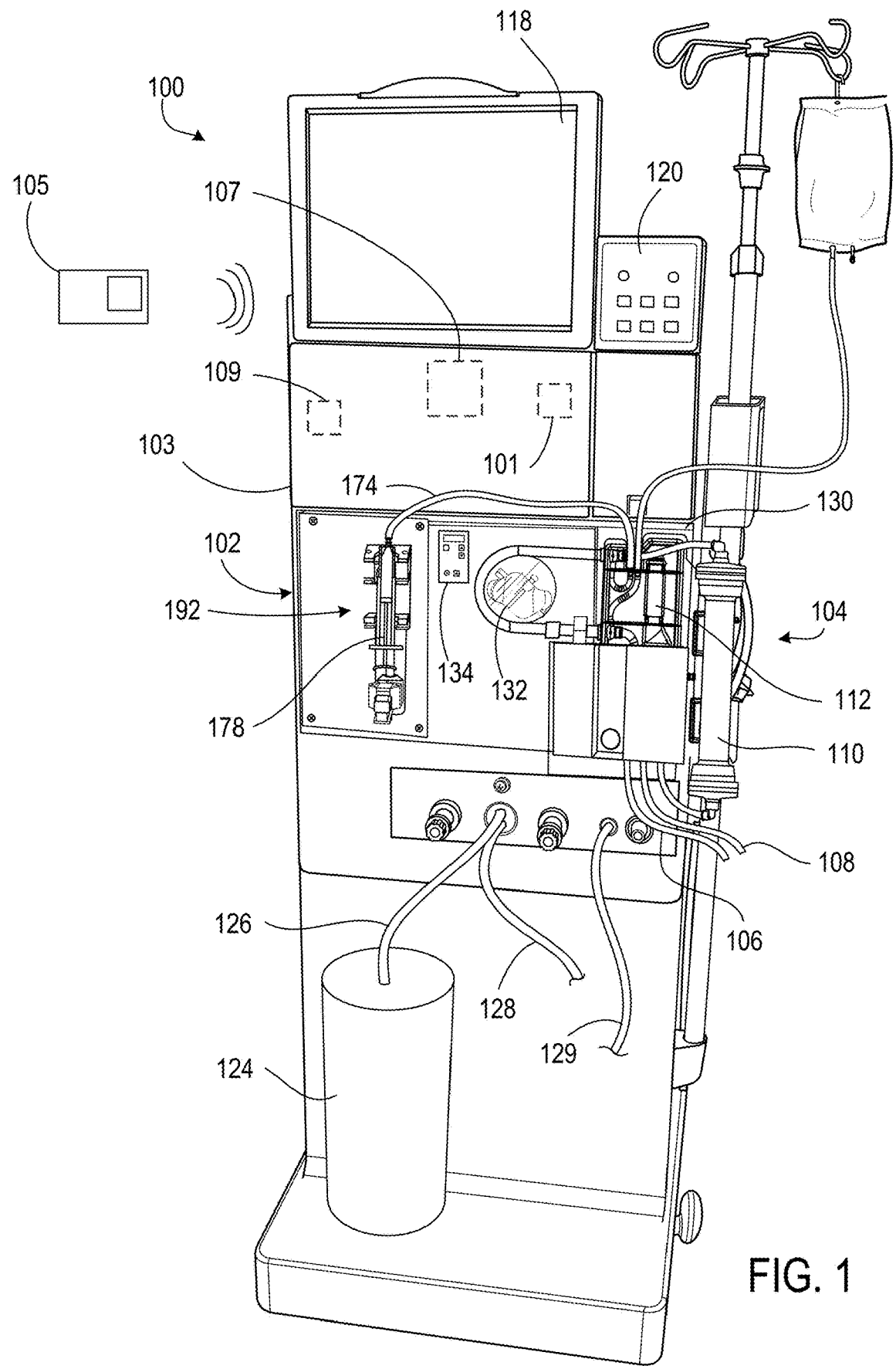
FIG. 1 is a front perspective view of a hemodialysis system that includes a communication module configured to communicate using a short-range wireless technology protocol.

FIG. 1 shows a dialysis system, such as a hemodialysis system 100, configured to wirelessly communicate with short-range wireless devices, such as an identification (ID) card 105. Although the system described herein is largely discussed in connection with hemodialysis systems by way of example, it is explicitly noted that the system described herein may be used in connection with other types of medical devices and treatments, including peritoneal dialysis (PD) systems. The hemodialysis system 100 includes a hemodialysis machine 102 connected to a disposable blood component set 104 that partially forms a blood circuit. During hemodialysis treatment, an operator connects arterial and venous patient lines 106, 108 of the blood component set 104 to a patient. The blood component set 104 includes an air release device 112, which contains a self-sealing vent assembly that allows air but does not allow liquid to pass. As a result, if blood passing through the blood circuit during treatment contains air, the air release device 112 will vent the air to atmosphere.

The blood component set 104 is secured to a module 130 attached to the front of the hemodialysis machine 102. The module 130 includes the blood pump 132 capable of circulating blood through the blood circuit. The module 130 also includes various other instruments capable of monitoring the blood flowing through the blood circuit. The module 130 includes a door that when closed, as shown in FIG. 1, cooperates with the front face of the module 130 to form a compartment that is sized and shaped to receive the blood component set 104. In the closed position, the door presses certain blood components of the blood component set 104 against corresponding instruments exposed on the front face of the module 130.

The operator uses a blood pump module 134 to operate the blood pump 132. The blood pump module 134 includes a display window, a start/stop key, an up key, a down key, a level adjust key, and an arterial pressure port. The display window displays the blood flow rate setting during blood pump operation. The start/stop key starts and stops the blood pump 132. The up and down keys increase and decrease the speed of the blood pump 132. The level adjust key raises a level of fluid in an arterial drip chamber.

The hemodialysis machine 102 further includes a dialysate circuit formed by the dialyzer 110, various other dialysate components, and dialysate lines connected to the hemodialysis machine 102. Many of these dialysate components and dialysate lines are inside the housing 103 of the hemodialysis machine 102 and are thus not visible in FIG. 1. During treatment, while the blood pump 132 circulates blood through the blood circuit, dialysate pumps (not shown) circulate dialysate through the dialysate circuit.

A dialysate container 124 is connected to the hemodialysis machine 102 via a dialysate supply line 126. A drain line 128 and an ultrafiltration line 129 also extend from the hemodialysis machine 102. The dialysate supply line 126, the drain line 128, and the ultrafiltration line 129 are fluidly connected to the various dialysate components and dialysate lines inside the housing 103 of the hemodialysis machine 102 that form part of the dialysate circuit. During hemodialysis, the dialysate supply line 126 carries fresh dialysate from the dialysate container 124 to the portion of the dialysate circuit located inside the hemodialysis machine 102. As noted above, the fresh dialysate is circulated through various dialysate lines and dialysate components, including the dialyzer 110, that form the dialysate circuit. As will be described below, as the dialysate passes through the dialyzer 110, it collects toxins from the patient's blood. The resulting spent dialysate is carried from the dialysate circuit to a drain via the drain line 128. When ultrafiltration is performed during treatment, a combination of spent dialysate (described below) and excess fluid drawn from the patient is carried to the drain via the ultrafiltration line 129.

The dialyzer 110 serves as a filter for the patient's blood. The dialysate passes through the dialyzer 110 along with the blood, as described above. A semi-permeable structure (e.g., a semi-permeable membrane and/or semi-permeable microtubes) within the dialyzer 110 separates blood and dialysate passing through the dialyzer 110. This arrangement allows the dialysate to collect toxins from the patient's blood. The filtered blood exiting the dialyzer 110 is returned to the patient. The dialysate exiting the dialyzer 110 includes toxins removed from the blood and is commonly referred to as "spent dialysate." The spent dialysate is routed from the dialyzer 110 to a drain.

A drug pump 192 also extends from the front of the hemodialysis machine 102. The drug pump 192 is a syringe pump that includes a clamping mechanism configured to retain a syringe 178 of the blood component set 104. The drug pump 192 also includes a stepper motor configured to move the plunger of the syringe 178 along the axis of the syringe 178. A shaft of the stepper motor is secured to the plunger in a manner such that when the stepper motor is operated in a first direction, the shaft forces the plunger into the syringe, and when operated in a second direction, the shaft pulls the plunger out of the syringe 178. The drug pump 192 can thus be used to inject a liquid drug (e.g., heparin) from the syringe 178 into the blood circuit via a drug delivery line 174 during use, or to draw liquid from the blood circuit into the syringe 178 via the drug delivery line 174 during use.

The hemodialysis machine 102 includes a user interface with input devices such as a touch screen 118 and a control panel 120. The touch screen 118 and the control panel 120 allow the operator to input various different treatment parameters to the hemodialysis machine 102 and to otherwise control the hemodialysis machine 102. The touch screen 118 displays information to the operator of the hemodialysis system 100. The touch screen 118 can also indicate whether the ID card 105 is in within communication range of the hemodialysis machine 102.

The hemodialysis machine 102 also includes a control unit 101 (e.g., a processor) configured to receive signals from and transmit signals to the touch screen 118, the control panel 120, and a communication module 107 (e.g., an NFC transceiver). The control unit 101 can control the operating parameters of the hemodialysis machine 102, for example, based at least in part on the signals received by the touch screen 118, the control panel 120, and the communication module 107. The communication module 107 is configured to communicate with a short-range wireless device using a short-range wireless technology protocol. For example, the communication module 107 allows the hemodialysis machine 102 to communicate with the ID card 105.

The control unit 101 is configured to identify presence of the ID card 105. For example, when the ID card 105 is within wireless communication range of the communication module 107, the communication module 107 can send a signal to the control unit 101 indicating that the ID card 105 is present. In response, the control unit 101 can cause the hemodialysis machine 102 to perform an action, as described in more detail below. Similarly, when the ID card 105 is taken out of wireless communication range of the communication module 107 (e.g., the ID card 105 goes from being in wireless communication range of the communication module 107 to not being in wireless communication range of the communication module 107), the communication module 107 can send a signal to the control unit 101 indicating that the ID card 105 is not present. In response, the control unit 101 can cause the hemodialysis machine 102 to perform an action.

Figure 2:
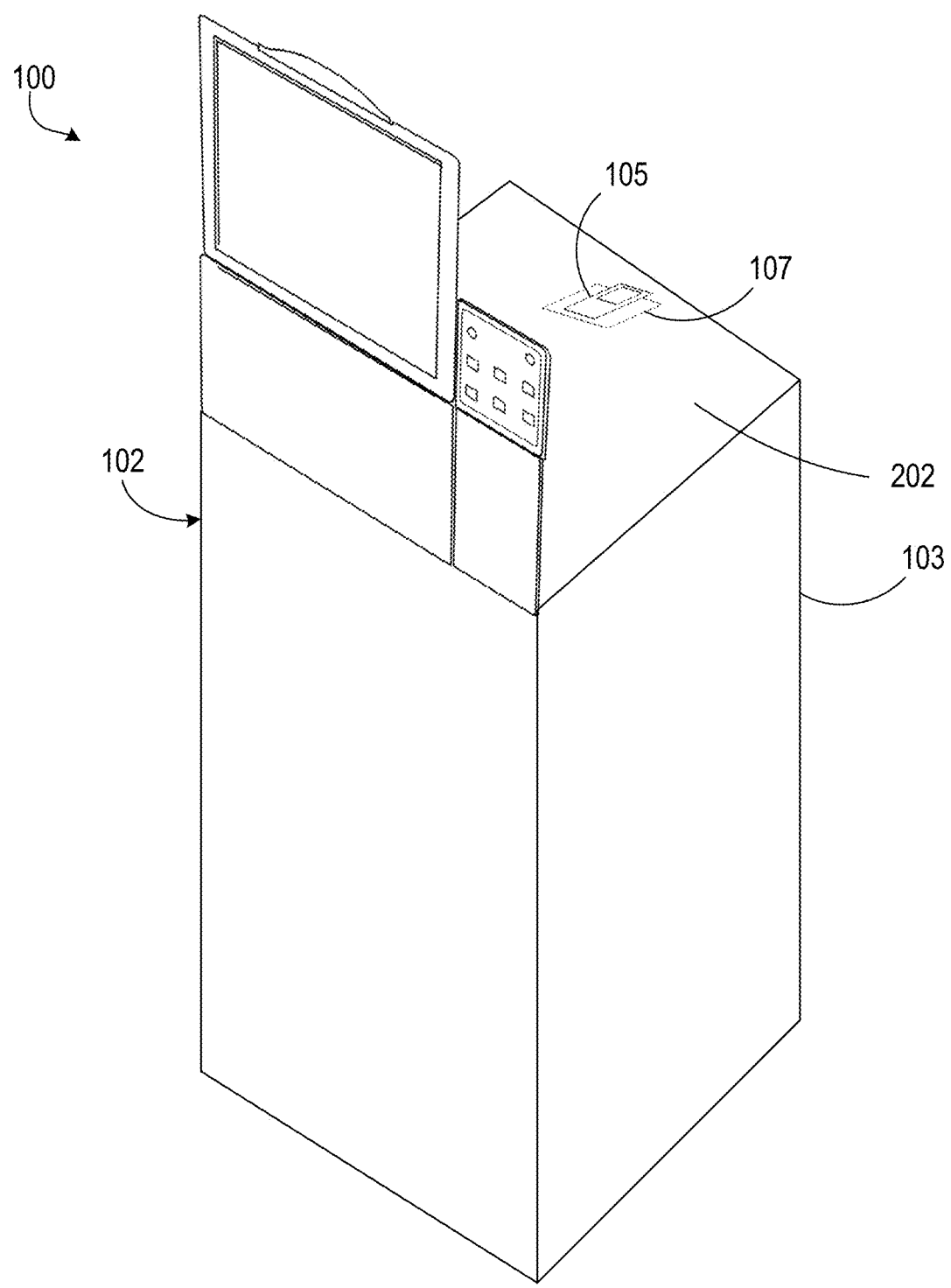
FIG. 2 shows an example of an ID card that is configured to communicate with the communication module of FIG. 1.

Referring to FIG. 2, the communication module 107 can be positioned at or near the top of the hemodialysis machine 102 such that the ID card 105 is within wireless communication range of the communication module 107 when the ID card 105 is placed on a surface 202 (e.g., a top surface) of the housing 103 of the hemodialysis machine 102. The communication module 107 is positioned within the housing 103 at a location substantially adjacent to the surface. In some implementations, the surface 202 includes a recess (not shown) in which the ID card 105 can rest such that the ID card 105 does not easily slide off of the surface with incidental contact.

The hemodialysis system 100 also includes a data storage configured to store data corresponding to identities of one or more short-range wireless devices, including the ID card 105. The data storage can be included as part of the hemodialysis machine 102 or may be remote from the hemodialysis machine 102 (e.g., on a server accessible by a computer network).

Figure 3:
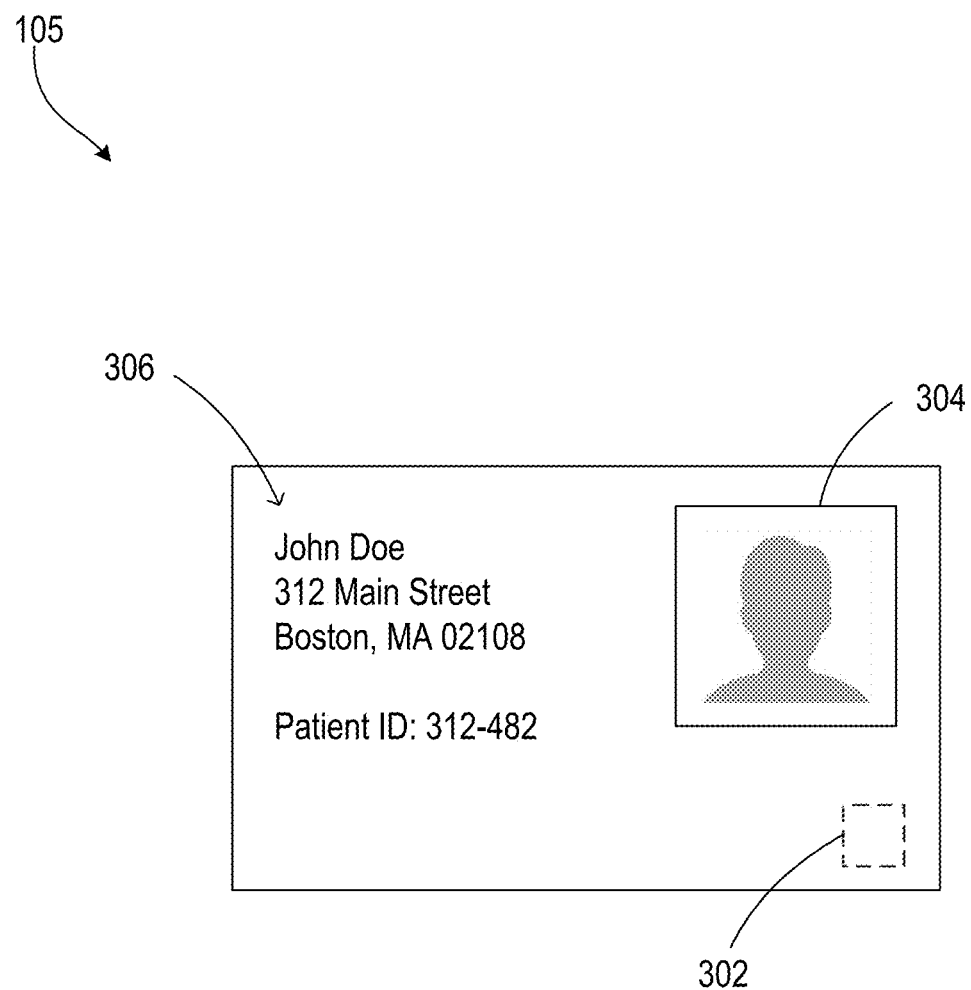
FIG. 3 is a side perspective view of the hemodialysis system of FIG. 1 in which the ID card of FIG. 2 is resting on top of a housing of the hemodialysis machine.

FIG. 3 shows an example of the ID card 105. The ID card 105 includes a communication module 302 (e.g., an NFC transceiver) that is configured to communicate with other communication modules using a short-range wireless technology protocol, such as the communication module 107 of the hemodialysis machine 102. The ID card 105 also includes a photo 304 of the person associated with the ID card and identification information 306. In this example, the ID card 105 is associated with a patient, and the identification information 306 includes the patient's name, the patient's address, and a patient identification number.

The communication modules 107, 302 are sometimes referred to as NFC initiators and NFC targets. NFC is a short-range wireless technology protocol that enables devices to establish radio communication amongst each other in order to quickly exchange data over a low latency link (e.g., a link which has relatively low delay between transmission and receipt of a portion of data such as a data packet or frame). Some implementations of NFC techniques are based on standards defined by the International Electrotechnical Commission and/or the International Organization for Standardization (ISO), for example, standards such as ISO 13157 and ISO 18092.

In some examples, the communication module 107 of the hemodialysis machine 102 may be an NFC initiator, and the communication module 302 of the ID card 105 may be an NFC target. For example, the ID card 105 may include a short-range communication technique, such as a contactless chip. Techniques for using contactless chips that could be used with the ID card 105 are defined in ISO 14443. The NFC initiator can generate an RF field that powers the NFC target when the NFC target is within operable range of the NFC initiator, thereby allowing the NFC target to provide data to the NFC initiator. In this way, the ID card 105 can provide information to the hemodialysis system 100.

The operable range of the NFC initiator and NFC target may be in the order of inches (e.g., 0-6 inches). In some implementations, the transfer of data is initiated upon the NFC initiator and the NFC target making physical contact with each other. In some implementations, the NFC initiator and/or the NFC target can include a motion sensor (e.g., an accelerometer) to assist in identifying the occurrence of physical contact between the modules.

The NFC initiator is sometimes part of another electronic device such as a mobile phone, a computer, or as in this example, a medical device. The NFC initiator can have an independent power source or it can receive power from a power source that provides power to the electronic device. The NFC initiator can include a loop antenna that uses magnetic induction to generate an RF field.

The NFC target (sometimes referred to as an NFC tag) is typically a passive module that relies on the power generated by the RF field to operate. The NFC target can include a memory that stores data to be provided to the NFC initiator. The NFC target can also include a loop antenna that is configured to modulate the RF field generated by the NFC initiator. The modulation is based at least in part on the stored data. The NFC initiator can identify characteristics of the modulated field, compare them to characteristics of the generated RF field, and use the comparison information to determine the data stored on the NFC initiator. Because the NFC target does not require its own power supply, the NFC target can take relatively simple form factors that can easily be incorporated into small portable devices, such as the ID card 105.

In some implementations, the NFC target is powered by its own power supply. In some examples, the NFC target can also generate an RF field, and the NFC initiator can modulate the RF field generated by the NFC target in a manner similar to that described above in order to provide data to the NFC target.

The NFC initiator and NFC target can transfer data at various speeds and according to various codings. For example, data can be transferred at speeds in the range of 100-500 kbit/s according to a delay encoding scheme or a phase encoding scheme. The NFC target and/or the NFC initiator can employ an amplitude modulation scheme (e.g., an amplitude-shift keying scheme) or a phase modulation scheme (e.g., a phase-shift keying scheme), among others, to modulate the generated RF field in order to convey information.

In the example illustrated in FIG. 3, the ID card 105 is configured to provide information related to the patient's identity to the hemodialysis system 100 when the ID card 105 is in proximity to (e.g., within wireless communication range of) the communication module 107. The information related to the patient's identity may be the patient's name and/or ID. In some implementations, the information related to the patient's identity is a value that corresponds to the patient's name and/or ID number, and the value is stored on the ID card 105. The hemodialysis system 100 can determine the patient's identity based on the received identification information. For example, the hemodialysis system 100 can access the data storage that stores data corresponding to identities of one or more short-range wireless devices, and use the patient's name and/or ID (or, e.g., the corresponding value) received from the ID card 105 to determine the identity of the patient. In response, the hemodialysis machine 102 can perform an action that is based at least in part on the identity of the patient.

In some implementations, the data corresponding to identities of one or more short-range wireless devices can include portions of patient records, such as each associated patient's name, address, phone number, identification number, and the like. The data corresponding to identities of one or more short-range wireless devices can include data representing the value that corresponds to the patient's name and/or ID number. The hemodialysis system 100 can query the data corresponding to identities of one or more short-range wireless devices using the patient name, ID, and/or value received from the ID card 105 to find the corresponding patient record and determine the identity of the patient. In various implementations, the data may be stored on the hemodialysis system 100 and periodically updated, such as via transmission using storage devices, e.g., having universal serial bus (USB) interfaces, that are transferred between the hemodialysis system 100 and a remote computer and/or site. In some implementations, the data may be obtained by the hemodialysis system 100 using real-time communication over a network, as described in further detail elsewhere herein.

The data corresponding to identities of one or more short-range wireless devices can also include information such as each associated patient's medical history, treatment prescriptions, treatment parameters, and the like. Examples of treatment parameters include a dialysate type, a dialysate fill volume, and a dialysate flow rate, to name a few. Upon determining that the ID card 105 belongs to a particular patient, the hemodialysis system 100 can identify a particular treatment that corresponds to that patient and cause the hemodialysis machine 102 to carry out an action. In some implementations, the action includes a dialysis treatment (e.g., the particular dialysis treatment that corresponds to the patient. For example, the hemodialysis system 100 can identify treatment parameters included in the dialysis treatment and identify particular values for those treatment parameters. The control unit 101 can cause the hemodialysis machine 102, including the dialyzer 110, to carry out the dialysis treatment based on the identified treatment parameters.

For example, suppose that the patient associated with the ID card 105, John Doe, has a medical condition that requires an atypical dialysis treatment. Perhaps John's treatment requires an abnormally low dialysate flow rate. The hemodialysis system 100 receives the patient identification information from the ID card 105, accesses the data storage, and uses the received patient identification information to identify medical information related to John. The medical information includes John's medical history, treatment prescriptions, and treatment parameters; in particular, the treatment prescription includes instructions for causing the hemodialysis machine 102 to employ the abnormally low dialysate flow rate that John requires. Such information is provided to the control unit 101, and the control unit 101 causes the appropriate treatment to be administered to John. For example, the control unit 101 can cause the hemodialysis machine 102 to operate the dialyzer 110 and/or operate a pump (e.g., a dialysate pump) such that the required dialysate flow rate is achieved.

As briefly mentioned above, in some implementations, the control unit 101 is configured to determine that the presence of the ID card 105 has ceased, and in response, cause the hemodialysis machine 102 to perform an action. The action may include a dialysis operation or be related to a dialysis operation. In some implementations, the dialysis operation includes initiation of a disinfection procedure, such as cleaning, rinsing, and/or other disinfection protocols.

In some implementations, the action includes an emergency and/or safety procedure. For example, the control unit 101 may determine that the presence of the ID card 105 has ceased before the normal (e.g., expected) termination of a treatment. In response, the control unit 101 can cause the hemodialysis machine 102 to carry out an emergency procedure that can include pausing and/or ceasing the dialysis treatment. For example, the control unit 101 may cause one or more pumps of the hemodialysis machine 102 to slow down and/or stop operating. In some implementations, the hemodialysis system 100 includes a user interface module that is configured to cause user interface elements (e.g., buttons) to be displayed on the touch screen 118. Upon determining that the presence of the ID card 105 has ceased, the control unit 101 may cause the user interface module to display a prompt to a user of the hemodialysis machine 102 to indicate whether to pause and/or cease the dialysis treatment. In some implementations, the dialysis treatment is not paused and/or ceased unless one or more conditions are satisfied. For example, the dialysis treatment may not be paused and/or ceased unless the hemodialysis system 100 determines that the patient is in a safe state.

In some implementations, the hemodialysis system 100 includes a network communication module 109. The network communication module 109 allows the hemodialysis system 100 to communicate with remote servers, computer systems, databases and/or other medical devices over a network such as a local area network (LAN) or the Internet. The network communication module 109 allows the hemodialysis system 100 to communicate with other medical devices, computer systems, servers, and/or databases associated with one or more medical facilities. The network communication module 109 may enable communication over the network using wired and/or wireless connections. For example, the network communication module 109 may enable communication using WiFi communication protocols and infrastructure and/or may enable communication using wireless mobile telecommunication networks. The system described herein may use appropriate encryption and security standards and protocols in connection with the transmission of sensitive and/or protected data in accordance with statutory and regulatory requirements.

In some implementations, the data corresponding to identities of one or more short-range wireless device is stored remote from the hemodialysis system 100. For example, the data corresponding to identities of one or more short-range wireless device can be stored on a computer system, server, and/or database that is associated with a medical facility corresponding to that of the hemodialysis system 100. The computer system, server, and/or database may be a medical database in which patient information is stored. In this way, the hemodialysis system 100 can receive portions of patient records from a remote location, e.g. obtained via communication over a network, when the ID card 105 is within wireless communication range of the communication module 107. The hemodialysis system 100 can then use the received information to identify the patient and determine the patient's medical history, treatment prescriptions, treatment parameters, and the like.

In some implementation, the hemodialysis system 100 transmits data when the presence of the ID card 105 has ceased. The data can include information related to the patient's dialysis treatment, such as treatment results and/or treatment details (e.g., treatment runtime, drugs administered, particular treatments/functions performed, etc.). In this way, information that is typically manually entered following a treatment can be automatically transmitted and stored. The data can be transmitted to the computer system, server, and/or database associated with the medical facility for storage. In some implementations, the data is transmitted and stored on a storage module of the ID card 105. The storage module may be part of or separate from the communication module 302. When the patient receives his or her next treatment, information related to the previous treatment can be provided to the hemodialysis system 100 and considered for determining an appropriate treatment. The storage module can also store the information related to the identity of the user (e.g., the patient's name, ID, and/or associated value).

Figure 4:
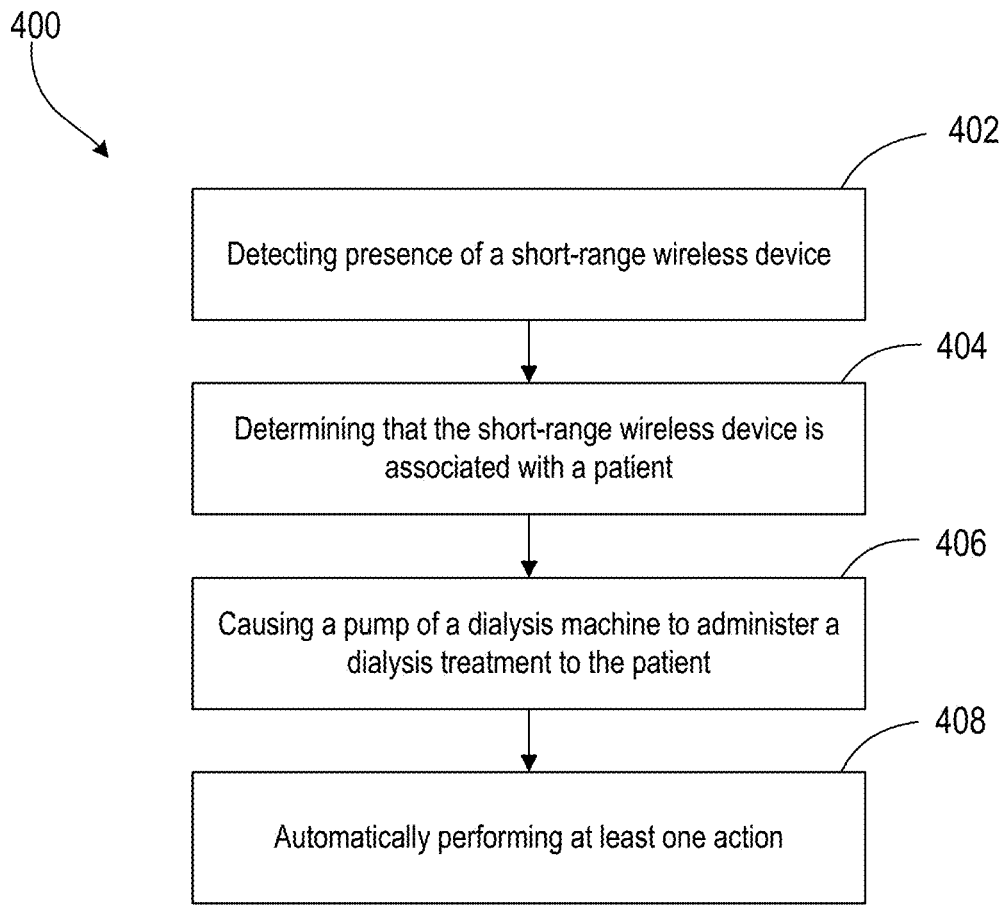
FIG. 4 is a flowchart depicting an example of performing dialysis.

FIG. 4 is a flowchart 400 depicting an example of performing dialysis. At step 402, presence of a short-range wireless device is detected using a short-range wireless technology protocol such as NFC. For example, when the ID card (105 of FIGS. 1-3) is within wireless communication range of the communication module 107, the communication module 107 can send a signal to the control unit 101 indicating that the ID card 105 is present.

At step 404, the short-range wireless device is determined to be associated with a patient. The ID card 105 can provide information related to the patient's identity to the hemodialysis system 100. The information related to the patient's identity can include the patient's name, the patient's ID, and/or a value that corresponds to the patient's name or ID. The hemodialysis system 100 can access data corresponding to identities of one or more ID cards, which can include portions of patient records, and use the patient's name, ID, and/or corresponding value to determine the identity of the particular patient associated with the particular ID card 105.

At step 406, a dialysis treatment is administered to the patient. The hemodialysis system 100 causes a pump of the hemodialysis machine 102 to administer the dialysis treatment. The pump may include a blood pump and/or a dialysate pump. In some implementations, the dialysis treatment is based at least in part on the data corresponding to identities of one or more ID cards, which can include medical histories, treatment prescriptions, and/or treatment parameters that correspond to patients associated with each ID card. In this way, the dialysis treatment may be tailored for the particular patient associated with the ID card 105.

At step 408, at least one action is automatically performed in response to one or both of i) determining that the short-range wireless device is present, and ii) determining that the short-range wireless device is no longer present. The action can include a dialysis operation, a data transmission, a cleaning/disinfecting procedure, and/or an emergency procedure (e.g., pausing, adjusting, or stopping operating of the pump). In some implementations, upon determining that the presence of the ID card 105 has ceased, the control unit 101 may cause a prompt to be displayed to a user of the hemodialysis machine 102 to indicate whether to perform the suggested action. In some implementations, the action is not performed unless one or more conditions are satisfied. For example, the action may not be performed unless the hemodialysis system 100 determines that the patient is in a safe state.

While certain implementations have been described, other implementations are possible.

In some implementations, the short-range wireless device (e.g., the ID card) is configured to communicate with other short-range wireless device, medical devices, and/or computer systems (including mobile computing devices). The short-range wireless device can receive information from or provide information to computing terminals in a medical facility. For example, a patient may introduce the short-range wireless device to a terminal to cause the information on the short-range wireless device to be updated. Information that can be updated includes the patient's record, medical history, treatment prescriptions, treatment parameters, and the like. The updated information can be provided by a medical database via the terminal. Similarly, information that is stored on the short-range wireless device, but which is not yet stored on the medical database, can be provided to the medical database via the terminal in order to update the patient's medical records. In some implementations, a patient may introduce the short-range wireless device to a mobile phone, a tablet, and/or any computing device configured to communicate with the short-range wireless technology protocol to receive and/or provide such information.

In some implementations, the hemodialysis system is configured to communicate, through the communication module, with other medical devices and/or medical accessories that utilize the short-range wireless technology protocol. For example, a medical supply, such as a supply of concentrate (e.g., a bicarbonate bag), can include a communication module that is configured to communicate with other communication modules using the short-range wireless technology protocol. The medical supply can also include a storage module that stores information related to the particular medical supply, such as the type and/or concentration of the bicarbonate. When the patient's ID card is introduced to the hemodialysis system, the system receives the patient's treatment prescriptions and treatment parameters. Such information can include the type and/or concentration of the bicarbonate that is to be used for the patient's treatment. When the medical supply is introduced to the hemodialysis system, the control unit can determine whether the identified medical supply matches that which is required for the patient's treatment. If the medical supply matches, the control unit allows the treatment to continue uninterrupted. However, if the medical supply does not match that which is required, the control unit may stop the treatment or provide an indication that the medical supply does not match.

While the communication module of the hemodialysis machine has been described as being positioned within the housing at a location adjacent to the surface of the housing, the communication module may be positioned elsewhere in the hemodialysis system. For example, the communication module may be positioned at or near the touch screen, the control panel, or a front surface of the housing.

While the communication modules and the short-range wireless devices have been described as using NFC, other short-range wireless technology protocols can also be used, such as radio-frequency identification (RFID) and/or Bluetooth™.

While the short-range wireless devices, medical devices, and medical accessories have been described as being configured to receive and provide information using the short-range wireless technology protocol, in some implementations, the device and/or accessory is configured to either provide information or receive information. For example, the medical supply may be configured to provide information related to the type and/or concentration of the bicarbonate without having the capability to receive and store information. Similarly, the ID card may be configured to provide information related to the patient without having the capability to receive and store information.

While the ID card has been described as including a photo and identification information of the person associated with the ID card, in some implementations, the ID card includes different or additional information. For example, the ID card may include information related to the patient's treatment prescription, insurance information, medical information (e.g., patient allergies), and the like.

In some implementations, the ID card includes one or more security components for verifying the identity of the person in possession of the ID card. For example, the ID card can include a biometric input module (e.g., a fingerprint reader) for verifying that the person in possession of the ID card is in fact the person with whom the card is associated. In this way, the likelihood of administering the wrong treatment to a patient is minimized.

In some implementations, information may not automatically be provided from the ID card to the communication module. Rather, a prompt may be provided upon the ID card being in wireless communication range of the communication module. The prompt may ask a user of the hemodialysis system to indicate the types of information that should be fetched. The user may instruct the hemodialysis system to fetch the patient's treatment prescription and use such information to suggest a dialysis treatment. On the other hand, the user may instruct the hemodialysis system to fetch the patient's medical history and records, and use such information to manually construct a dialysis treatment. Providing such a prompt can ensure that treatments are not applied to the patient without review and/or approval. Further, the prompt can eliminate a scenario in which a patient receives the wrong dialysis treatment because a person who is not receiving the treatment accidentally introduces his or her ID card to the hemodialysis machine.

While the dialysis system has been largely described as being a hemodialysis system, other medical treatment systems can employ the techniques described herein. Examples of other medical treatment systems include peritoneal (PD) dialysis systems, hemofiltration systems, hemodiafiltration systems, apheresis systems, and cardiopulmonary bypass systems.

Figure 5:
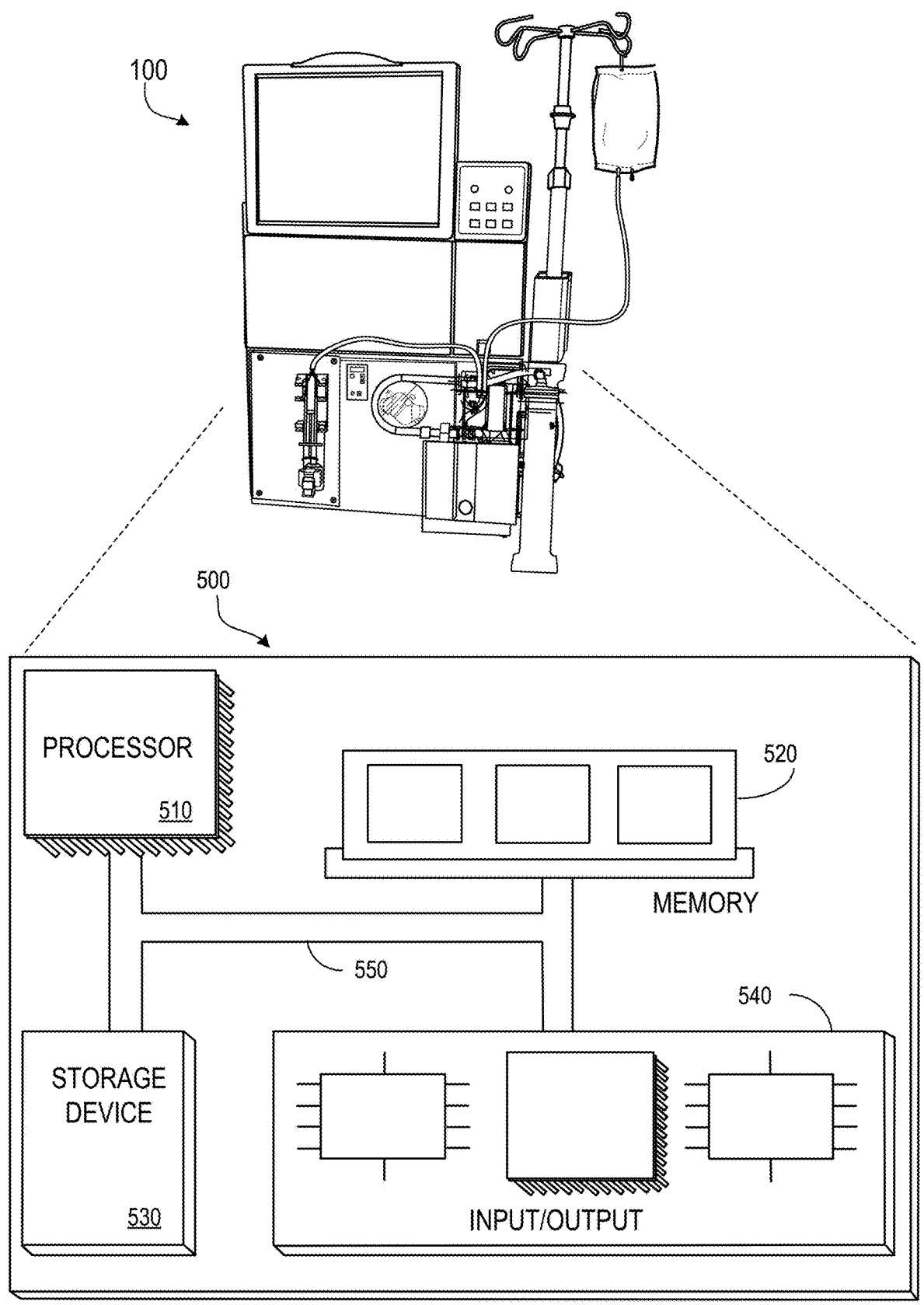
FIG. 5 shows an example of a computer system.

FIG. 5 is a block diagram of an example computer system 500. For example, referring to FIG. 1, the control unit 101 could be an example of the system 500 described here. The system 500 includes a processor 510, a memory 520, a storage device 530, and an input/output device 540. Each of the components 510, 520, 530, and 540 can be interconnected, for example, using a system bus 550. The processor 510 is capable of processing instructions for execution within the system 500. The processor 510 can be a single-threaded processor, a multi-threaded processor, or a quantum computer. The processor 510 is capable of processing instructions stored in the memory 520 or on the storage device 530. The processor 510 may execute operations such as causing the dialysis system to carry out functions related to voice commands, voice alarms, and voice instructions.

The memory 520 stores information within the system 500. In some implementations, the memory 520 is a computer-readable medium. The memory 520 can, for example, be a volatile memory unit or a non-volatile memory unit. In some implementations, the memory 520 stores information related to patients' identities. The information related to patients' identities can include patient names, identification numbers, or values that correspond to patient names or identification numbers, among others.

The storage device 530 is capable of providing mass storage for the system 500. In some implementations, the storage device 530 is a non-transitory computer-readable medium. The storage device 530 can include, for example, a hard disk device, an optical disk device, a solid-date drive, a flash drive, magnetic tape, or some other large capacity storage device. The storage device 530 may alternatively be a cloud storage device, e.g., a logical storage device including multiple physical storage devices distributed on a network and accessed using a network. In some implementations, the information stored on the memory 520, such as the information related to patients' identities, can also or instead be stored on the storage device 530.

The input/output device 540 provides input/output operations for the system 500. In some implementations, the input/output device 540 includes one or more of network interface devices (e.g., an Ethernet card), a serial communication device (e.g., an RS-232 10 port), and/or a wireless interface device (e.g., a short-range wireless communication device, an 802.11 card, a 3G wireless modem, or a 4G wireless modem). In some implementations, the input/output device 540 includes driver devices configured to receive input data and send output data to other input/output devices, e.g., a short-range wireless communication device (such as the ID card 105), a keyboard, a printer, and display devices (such as the touch screen display 118). In some implementations, mobile computing devices, mobile communication devices, and other devices are used.

In some implementations, the input/output device 540 includes a communication module (e.g., the communication module 107 of FIG. 1) that is configured to communicate using a short-range wireless technology protocol. For example, the communication module may be an NFC initiator that can establish radio communication with an NFC target (e.g., the NFC target of the ID card 105).

The NFC initiator can include a loop antenna that is configured to generate an RF field that powers the NFC target when the NFC target is within wireless communication range of the NFC initiator. The NFC target can also include a loop antenna that is configured to modulate the generated RF field based on stored data in order to provide the data to the NFC initiator. For example, the NFC initiator can identify characteristics of the modulated field, compare them to characteristics of the generated RF field, and use the comparison information to determine the stored data. In some implementations, the identification and comparison is performed by the processor 510. The data provided by the NFC target may be stored on the memory 520, the storage device 530, or a separate storage local to the NFC target, among others. In some implementations, the data provided to the NFC initiator can be used to determine an identity of a user associated with the NFC target.

In some implementations, the system 500 is a microcontroller. A microcontroller is a device that contains multiple elements of a computer system in a single electronics package. For example, the single electronics package could contain the processor 510, the memory 520, the storage device 530, and input/output devices 540.

Although an example processing system has been described in FIG. 5, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments of the invention have been described. Nevertheless, it will be understood that various modifications may be made without departing from the spirit and scope of the invention. Accordingly, other embodiments are within the scope of the following claims.

What is claimed is:

1. A dialysis system comprising:
   a dialysis machine;
   a communication module configured to communicate using a short-range wireless technology protocol;
   data storage configured to store user data, the user data indicating:
      a plurality of user identities, each user identity corresponding to a user of one or more short-range wireless devices; and
      one or more treatment parameters corresponding to each user identity of the plurality of user identities; and
   a processor configured to:
      identify presence of a short-range wireless device;
      determine, based on the short-range wireless device, at least one user identity of the plurality of user identities, and
      automatically cause the dialysis machine to carry out at least one mechanical action in response to one or both of i) the presence of the short-range wireless device being identified, and ii) the presence of the short-range wireless device being no longer identified, wherein automatically causing the dialysis machine to carry out the at least one mechanical action comprises:
         identifying, based on the user data stored in the data storage, the one or more treatment parameters corresponding to the at least one user identity; and
         initiating a dialysis treatment in accordance with the identified one or more treatment parameters.

2. The dialysis system of claim 1, wherein the short-range wireless device comprises a communication module configured to communicate with the communication module of the dialysis system.

3. The dialysis system of claim 1, wherein the at least one mechanical action comprises initiating a disinfection procedure.

4. The dialysis system of claim 1, wherein initiating the dialysis treatment comprises initiating an atypical dialysis treatment.

5. The dialysis system of claim 1, wherein the dialysis machine is configured to operate a pump of the dialysis system, and wherein the at least one mechanical action comprises operation of the pump.

6. The dialysis system of claim 1, wherein the one or more treatment parameters comprise one or more of a dialysate type, a dialysate fill volume, and a dialysate flow rate.

7. The dialysis system of claim 1, wherein the processor is configured to determine that the presence of the short-range wireless device has ceased, and in response, automatically carry out the at least one mechanical action.

8. The dialysis system of claim 7, wherein the processor is configured to:
   determine that the presence of the short-range wireless device has ceased before an expected termination of the at least one mechanical action; and
   in response to determining that the presence of the short-range wireless device has ceased before the expected termination of the at least one mechanical action, carry out an emergency procedure.

9. The dialysis system of claim 8, wherein the emergency procedure comprises one or both of pausing and ceasing the dialysis treatment.

10. The dialysis system of claim 7, wherein the at least one mechanical action comprises stopping operation of a pump of the dialysis system.

11. The dialysis system of claim 1, wherein the processor is further configured to transmit data representing information about a patient undergoing a dialysis treatment.

12. The dialysis system of claim 11, wherein the data is transmitted to and stored on the short-range wireless device.

13. The dialysis system of claim 1, comprising:
   a user interface module, wherein the user interface module is configured to prompt a user of the dialysis system to indicate whether to cease the dialysis treatment.

14. The dialysis system of claim 1, wherein the short-range wireless device comprises an identification card.

15. The dialysis system of claim 14, wherein the dialysis machine includes a housing, the housing having a surface that allows the identification card to rest thereon, wherein the communication module is within the housing at a location substantially adjacent to the surface.

16. The dialysis system of claim 14, wherein the identification card includes a photograph of a person associated with the identification card.

17. The dialysis system of claim 1, wherein the communication module is configured to communicate using one or more of a Near-Field Communication (NFC) protocol, an RFID protocol, and a Bluetooth™ protocol.

18. The dialysis system of claim 1, wherein the user data comprises data associated with one or more values stored on the one or more short-range wireless devices.

19. The dialysis system of claim 1, wherein the user data comprises data indicating at least a portion of a patient record of a patient who will undergo a dialysis treatment.

20. The dialysis system of claim 19, wherein the portion of the patient record comprises a name of the patient.

21. The dialysis system of claim 19, comprising:
a network communication module, wherein the data storage is configured to receive the portion of the patient record by way of the network communication module, and wherein the portion of the patient record originates at a computer system of a medical facility.

22. The dialysis system of claim 1, wherein the processor is configured to determine that the short-range wireless device corresponds to a medical supply associated with the dialysis treatment.

23. The dialysis system of claim 1, wherein the dialysis treatment comprises a hemodialysis treatment.

24. The dialysis system of claim 1, wherein the dialysis treatment comprises a peritoneal dialysis treatment.

25. A method of performing dialysis, comprising:
detecting, using a short-range wireless technology protocol, presence of a short-range wireless device;
determining that the short-range wireless device is associated with a patient;
retrieving, from data storage and based on the identity of the patient, one or more treatment parameters corresponding to the patient;
and
automatically causing the dialysis machine to perform at least one mechanical action in response to one or both of i) determining that the short-range wireless device is present, and ii) determining that the short-range wireless device is no longer present, wherein automatically causing the dialysis machine to carry out the at least one mechanical action comprises initiating a dialysis treatment in accordance with the identified one or more treatment parameters.

26. The method of claim 25, wherein the short-range wireless device comprises an identification card of the patient.

27. The method of claim 25, wherein the at least one mechanical action comprises causing a pump to administer the dialysis treatment.

28. The method of claim 25, where the one or more treatment parameters comprises one or more of a dialysate type, a dialysate fill volume, and a dialysate flow rate.

29. The method of claim 25, comprising:
transmitting data representing information about the patient.

30. The method of claim 29, wherein the data is transmitted to and stored on the short-range wireless device.

31. A dialysis system comprising:
a dialysis machine;
a communication module configured to communicate using a short-range wireless technology protocol;
data storage configured to store user data the user data indicating:
a plurality of user identities, each user identity corresponding to a user of one or more short-range wireless devices; and
one or more treatment parameters corresponding to each user identity of the plurality of user identities; and
a processor configured to:
identify presence of a short-range wireless device;
determine, based on the short-range wireless device, at least one user identity of the plurality of user identities
cause the dialysis machine to carry out at least one mechanical action when one or both of i) the presence of the short-range wireless device is identified, and ii) the presence of the short-range wireless device is no longer identified;
determine that the presence of the short-range wireless device has ceased, and in response, automatically carry out the at least one mechanical action;
determine that the presence of the short-range wireless device has ceased before an expected termination of the at least one mechanical action;
determine that a patient receiving a treatment from the dialysis machine is in a safe state; and
in response to determining that the presence of the short-range wireless device has ceased before the expected termination of the action and that the patient is in a safe state, automatically carry out an emergency procedure
wherein causing the dialysis machine to carry out the at least one mechanical action comprises:
identifying, based on the user data stored in the data storage, the one or more treatment parameters corresponding to the at least one user identity; and
initiating a dialysis treatment in accordance with the identified one or more treatment parameters.

32. A dialysis system comprising:
a dialysis machine;
a communication module configured to communicate using a short-range wireless technology protocol;
data storage configured to store user data, the user data indicating:
a plurality of user identities, each user identity corresponding to a user of one or more short-range wireless devices; and
one or more treatment parameters corresponding to each user identity of the plurality of user identities; and
a processor configured to:
identify presence of a short-range wireless device;
determine, based on the short-range wireless device, at least one user identity of the plurality of user identities;
automatically cause the dialysis machine to carry out at least one mechanical action in response to one or both of i) the presence of the short-range wireless device being identified, and ii) the presence of the short-range wireless device being no longer identified; and
determine that the presence of the short-range wireless device has ceased, and in response, automatically carry out the at least one mechanical action, wherein automatically causing the dialysis machine to carry out the at least one mechanical action comprises:
identifying, based on the user data stored in the data storage, the one or more treatment parameters corresponding to the at least one user identity; and
initiating a dialysis treatment in accordance with the identified one or more treatment parameters; and
wherein the at least one mechanical action comprises stopping operation of a pump of the dialysis system.

* * * * *